US005759858A

United States Patent [19]

Nieuwenhuizen

[11] Patent Number: 5,759,858
[45] Date of Patent: Jun. 2, 1998

[54] CALIBRATOR AND USE THEREOF IN AN IMMUNOASSAY

[75] Inventor: Willem Nieuwenhuizen, Bunnik, Netherlands

[73] Assignee: Akzo Nobel N.V., Arnhem, Netherlands

[21] Appl. No.: 603,698

[22] Filed: Feb. 20, 1996

Related U.S. Application Data

[63] Continuation of Ser. No. 317,408, Oct. 3, 1994, abandoned, which is a continuation of Ser. No. 18,615, Feb. 17, 1993, abandoned.

[30] Foreign Application Priority Data

Feb. 17, 1992 [EP] European Pat. Off. ............ 92200439

[51] Int. Cl.[6] ................... G01N 33/96; G01N 33/68; G01N 33/53
[52] U.S. Cl. ................. 436/16; 436/15; 435/7.94; 435/13; 435/963; 435/967; 530/382; 530/856
[58] Field of Search .................. 435/7.9, 7.94, 435/13, 963, 967; 436/15, 16; 530/382, 856

[56] References Cited

U.S. PATENT DOCUMENTS

| | | | |
|---|---|---|---|
| 4,376,110 | 3/1983 | David et al. | 435/7.94 |
| 4,692,406 | 9/1987 | Becker et al. | 435/13 |
| 5,099,004 | 3/1992 | Nieuwenhuizen | 435/13 |
| 5,116,950 | 5/1992 | Miyano et al. | 530/382 |
| 5,188,940 | 2/1993 | Krause et al. | 435/13 |

FOREIGN PATENT DOCUMENTS

| | | |
|---|---|---|
| 0070478 | 1/1983 | European Pat. Off. . |
| 0137269 | 4/1985 | European Pat. Off. . |
| 0152612 | 8/1985 | European Pat. Off. . |
| 0189910 | 8/1986 | European Pat. Off. . |
| 91/01497 | 2/1991 | WIPO ................ 436/16 |

OTHER PUBLICATIONS

Scheefers–Borchel et al, 1985. Discrimination Between Fibrium and Fibrinogen by a Monoclonal Antibody Against a Synthetic Peptide. Proc. Natl. Acad. Sci. 82:7091–5.

Brosstad et al, 1977. Same Characteristics of Various Fibrium Monomer Preparations Made from Dissolved Fibrium Clots. Haemostasis 6:213–24.

*Primary Examiner*—Paula K. Hutzel
*Assistant Examiner*—James L. Grun
*Attorney, Agent, or Firm*—Sharon N. Klesner; Mary E. Gormley

[57] ABSTRACT

The invention relates to a composition comprising among others a fibrinopeptide A releasing compound. Furthermore the invention relates to the use of the composition as calibrator in plasma containing fibrinogen. A test kit comprising the said composition and a method to determine soluble fibrin also belong to the invention.

9 Claims, No Drawings

CALIBRATOR AND USE THEREOF IN AN IMMUNOASSAY

This is a continuation of U.S. patent application Ser. No. 08/317,408, filed Oct. 3, 1994, now abandoned, which is a file wrapper continuation of U.S. patent application Ser. No. 08/018,615, filed Feb. 17, 1993, now abandoned.

The invention relates to a composition comprising among others a fibrinopeptide A releasing compound.

The invention also relates to the use of the composition as calibrator in plasma containing fibrinogen.

A test kit comprising the said composition and a method to determine soluble fibrin in plasma also belong to the invention.

BACKGROUND OF THE INVENTION

Thrombosis is a serious and often fatal disease in which blood clots (thrombi) interfere with the normal flow of blood in blood vessels or the heart. Fibrin is a protein generated by the action of the blood coagulation protein thrombin on fibrinogen. A thrombus is a deposit of blood components, such as fibrin with red blood cells and/or aggregated platelets in a blood vessel or cavity of the heart. A thrombus includes insoluble fibrin polymers that are later decomposed through fibrinolysis. Thrombi can obstruct normal blood flow, leading to serious and often fatal consequences.

Other disorders also exhibit an increased tendency to thrombosis. These include, but are not limited to cancer, pregnancy, aging, trauma, oral contraceptive use, diabetes mellitus, liver and kidney disease, obesity, and major surgical interventions such as elective hip replacement in elderly people.

Minimizing the risk of thrombosis to patients by anticoagulant therapy is a frequently applied treatment in the field. When an anticoagulant is administered, it is necessary to determine the desired levels of the drug to maintain effective therapy. Currently the appropriate dosage for oral anticoagulant therapy is established by monitoring the patient's prothrombin time ("PT"), which is maintained at approximately one and one-half to two and one-half times that obtained with normal plasma. The approximate dosage for heparin therapy is often established by monitoring the patient's activated partial thromboplastin time ("APTT"), which is maintained higher than 1.5 times the control.

Blood coagulation is a highly complex process, not totally understood even today. The final stage of the coagulation pathway results in the formation of fibrin, a component required for thrombus formation. Prothrombin activation and the associated generation of thrombin are required for fibrin formation.

Fibrin formation is a multistep process, which is initiated by thrombin. First thrombin, the product of an activated coagulation system, will release fibrinopeptides A from the amino-terminal ends of the two fibrinogen Aα-chains.

Simultaneously, but more slowly, fibrinopeptides B are released from the amino-terminal ends of the two fibrinogen Bβ-chains. As a result of the release of the fibrinopeptides, new amino-terminals are exposed on the fibrin α- (and β-) chains, which bind to complementary sites already present in fibrinogen. Thus, these fibrin molecules form soluble complexes with fibrinogen.

These complexes are, therefore, designated as soluble fibrin (complexes). Beyond a certain fibrin concentration the fibrin moieties will segregate from the complexes and aggregate to form a macroscopic gel in which the fibrin subunits will be crosslinked by factor XIII, activated by thrombin.

Soluble fibrin has received considerable attention as a molecular marker for intravascular fibrin formation, and impending thrombotic events.

Several assays for soluble fibrin have been described. These include paracoagulation-based assays such as the ethanol gelation test, the serial dilution protamine sulphate test, and the ristocetin precipitation test.

The latter methods, which are based upon milieu alterations suffer from rather low sensitivity and limited specificity, and give only qualitative results. Other types of assay are based upon the agglutination of erythrocytes coated with fibrin in the presence of soluble fibrin, gel exclusion chromatography and adsorption of soluble fibrin to immobilized fibrinogen and fibrin.

The existing methods are qualitative, semi-quantitative or laborious and time-consuming, which makes them less suitable for routine clinical applications. Moreover their specificity is rather limited. An EIA, which is based on a combination of highly specific monoclonal antibodies ("MoAb") could overcome these shortcomings as has been shown, for example, by Scheefers-Borchel et al. (1985), Proc. Natl. Acad. Sci. USA Vol. 82 pp. 7091–7095. Their EIA (enzyme immunoassy) however consists of a MoAb, specific for a neo-epitope, expressed by soluble fibrin and some fibrin degradation products i.e. Aα-[17–22], in combination with a HRP conjugate of polyclonal antibodies against fibrin(ogen)-related material. On the basis of these specificities soluble fibrin degradation products comprising that epitope are also expected to be detected.

In above-mentioned routine clinical applications there is often a need to exactly analyze the amount of fibrin in the blood of a patient at risk for a thrombotic complication.

A necessity is that at each time the amount of soluble fibrin in the blood sample must be detected in a quantitative manner in order to predict if and when thrombosis will occur.

A special problem is the preparation of a well-defined calibrator. One option is the partial conversion of plasma fibrinogen by the treatment of plasma for a short period of time with a low concentration of thrombin as had been used by others (Scheefers-Borchel et al., 1985). However, in that case the concentration of soluble fibrin in the calibrator has to be assessed indirectly for each batch by the measurement of the concentration of released fibrinopeptides A.

It is our invention in order to avoid this problem to convert all fibrinogen in a plasma with a known fibrinogen concentration, to fibrin under conditions where fibrin remains in solution.

Surprisingly a composition comprising fibrinogen, sugar alcohol, preservative, metal halogenide, amino acid and a fibrinopeptide A releasing compound shows a solution to this problem.

Preferably a composition wherein the sugar alcohol is mannitol, the preservative is sodium azide, the metal halogenide is sodium bromide and the amino acid is glycine and optionally the fibrinopeptide A releasing compound such as the enzyme Arvin® can be used.

Arvin® is an enzyme from the venom of Agkistrodon rhodostoma which releases only fibrinopeptides A from fibrinogen. Instead of Arvin also Batroxobin or Reptilase can be used. Furthermore instead of mannitol other sugar alcohols can be used such as glucitol, sorbitol, glycerol or inositol.

Most preferably is a composition according to the invention wherein an Arvin inactivating compound is present such

3 as anti-Arvin antibodies or so-called peptide chloroketones which attack the active site of the enzyme used.

Part of the invention is the use of said composition as calibrator in plasma containing fibrinogen, wherein optionally a thrombin inhibitor is present, such as heparin, hirudin or PPACK.

For said intended use a buffer containing mannitol, glycine, sodium azide, sodium phosphate and sodium bromide is prepared preferably as follows, per liter buffer: 13 g mannitol, 7.5 g glycine, 10 g sodium azide, 9.0 g $NaH_2PO_4 \cdot 2H_2O$, 1.4 g $Na_2HPO_4$ and 102.9 g sodium bromide, with pH =7.4.

Normal plasma with a known fibrinogen concentration was diluted (to give a final fibrinogen concentration of 40 µg/ml) with said buffer.

This diluted plasma was then treated with Arvin (final concentration 0.27 IU/ml) for 2 hours. During this incubation step all fibrinogen is converted to fibrin, as was confirmed by the EIA procedure described below, i.e. no further increase in response occurred upon longer incubation or upon further addition of Arvin. Arvin activity was blocked by the addition of polyclonal anti-Arvin antiserum to the clear solution. The total conversion of fibrinogen was further confirmed by the complete loss of reactivity in another EIA (for fibrinogen).

As a consequence of the complete conversion, the concentration of soluble fibrin in this solution, further refer to as stock solution, equals that of the fibrinogen originally present.

The composition is filled in aliquots in siliconized glass tubes and lyophilized. Before use, the lyophilized calibrator optionally present in a test kit according to the invention can be reconstituted in PBS/Tween® without any problem.

In order to determine in a reproducible and reliable manner the soluble fibrin in plasma, an EIA for the quantitative determination of said soluble fibrin was developed which does not detect fibrin(ogen) degradation products.

The following example shows that such enzyme immunoassay using the composition according to the invention as calibrator is very suitable for routine clinical applications and monitoring of the effectivity of heparinization.

EXAMPLE

Materials

Microtitre plates (Immulon, Dynatech) were purchased from Greiner, Alphen a/d Rijn, The Netherlands; 3,3',5,5'-tetramethylbenzidin (TMB) from Fluka (Buchs, Switzerland); N-succinimidyl-3-(2-pyridyldithio)propionate (SPDP), protein A Sepharose and Sephacryl S-200 were from Pharmacia (Uppsala, Sweden) and dimethylsulphoxide (DMSO) from Baker Chemical Company (Philipsburg, U.S.A.). Horse-radish peroxidase (HRP, grade II) from Boehringer Mannheim (Mannheim, Germany). Arvin (an enzyme from the venom of *Agkistrodon rhodostoma*), which releases only fibrinopeptides A from fibrinogen, and anti-Arvin antiserum which blocks all Arvin activity were generous gifts of Knoll (Ludwigshafen, Germany).

PPACK (D-Phenylalanyl-L-Prolyl-L-Arginine chloromethyl-ketone), 2.5 TFA (Trifluoro acetic acid) was purchased from Calbiochem Corp. (La Jolla, Calif.).

Test kits based upon the rate-enhancing effects of soluble fibrin on the t-PA mediated plasminogen activation, "COA-SET Fibrin monomer", were obtained from KABI (Uppsala, Sweden).

4

Test kits for fibrinopeptide A (RIA-mat® FPA) were obtained from Byk-Sangtec Diagnostica, Dietzenbach, Germany.

Tween-containing phosphate-buffered saline (PBST) was prepared by dissolving 1.4 g $Na_2HPO_4$, 0.215 g $KH_2PO_4$, 8.75 g NaCl and 0.5 ml Tween 20 in 1 liter of distilled water.

$TMB/H_2O_2$ substrate solution was prepared as follows: 100 µl of a 42 mM solution of TMB in DMSO was added to 10 ml of a 0.1M sodium acetate/citric acid buffer pH 6.0 under constant agitation. Just before use 1.5 µl $H_2O_2$ (30% w/v) was added.

Antibodies

Fibrin-specific monoclonal antibody anti-Fb-½ (epitope in Aα-[148–160]) was used. It is an IgM, with kappa light chains, which is easily purified from ascites by gel filtration on a Sephacryl S-200 column (30×3.0 cm) equilibrated with 0.005M phosphate buffer pH 6.0. Anti-Fb-½ containing ascites was applied to the column. The column was washed with at least four column volumes, until the absorbance of the eluate was ≦0.02. Then virtually pure anti-Fb-½ was eluted with 0.05M phosphate buffer, containing 1.4M NaCl, pH 6.0.

Monoclonal antibody G8 (epitope in carboxyl-terminal domain of the Aα-chains) was used. It is of the IgG1 class with kappa light chains. It was purified from ascites fluid by using protein A Sepharose.

Conjuqation of MoAb G8 with HRP

Purified MoAb G8 was conjugated as described in the Pharmacia booklet on SPDP. The conjugate was purified from the remaining free HRP by passing the conjugation mixture over a Sephacryl S-200 column (150×1.2 cm) run in 0.3M NaCl. The conjugate-containing fractions were pooled and kept frozen at −80° C. The conjugate (G8/HRP) was diluted prior to use with PBST containing 0.5% (w/v) BSA (PBST/BSA) to the appropriate concentration.

Coating of Microtitre Plates

Purified MoAb anti-Fb-½ was diluted in 0.05M phosphate pH 7.4 to give a final concentration of 10 µg/ml. Aliquots of 135 µl of this solution were pipetted into the wells of microtitre plates and incubated overnight at 4° C. After this incubation the wells were emptied, washed with PBST, and used.

Calibration Material

The preparation of the calibrator has already been mentioned above in this application.

Since we wished to use dilutions of the stock solution in a plasma milieu as the eventual calibrator in the EIA, and since plasma may already contain (low) unknown concentrations of soluble fibrin (the normal range is 0.5–13 µg/ml); the concentration of soluble fibrin present in this plasma pool was determined as follows.

Dose-response curves of serial two-fold dilutions of five-fold diluted plasma, and of the same plasma to which calibrator stock solution had been added to increase the concentrations by 2, 4 and 6 µg/ml (by addition of 0.05, 0.100 and 0.150 ml stock solution to 1 ml plasma, respectively) run parallel in the EIA described below. If plasma contains x µg soluble fibrin/ml, the 5-, 10-, 20- and 40-fold diluted plasma will contain 0.2 x , 0.1 x, 0.05 x, 0.025 x µg/ml, respectively. The spiked plasma dilutions will contain $$0.2\frac{(x+2)}{1+0.05}, 0.1\frac{(x+2)}{1+0.05} \ldots ; 0.2\frac{(x+4)}{1+0.1}, 0.1\frac{(x+4)}{1+0.1} \ldots ;$$

$$0.2\frac{(x+6)}{1+0.15}, 0.1\frac{(x+6)}{1+0.15} \ldots \mu g/ml,$$

respectively.

When e.g. the response for 0.2 x (5-fold diluted non-spiked plasma) equals $$0.1\frac{(x+2)}{1+0.05}$$

(plasma spiked with 2 µg/ml at 10-fold dilution), $$0.2x = 0.1\frac{(x+2)}{1+0.05}$$

thus x=1.8 µg/ml.

Using this procedure we established that our plasma pool contained 2.4 µg soluble fibrin/ml.

The normal plasma pretreated with PPACK (0.05 ml of a 5 mM solution per ml of plasma) was then adjusted with fibrin stock solution to a final concentration of 5 µg/ml. This is the calibrator for the EIA described below.

EIA Procedure

A five-fold dilution of the calibrator was made in PBST to which 5 IU heparin/ml was added (PBST/hep). Subsequently 10-, 20-, 40- and 80-fold dilutions were made by serial two-fold dilutions in PBST/hep. Test samples were routinely diluted 5- and 10-fold in PBST/hep. Aliquots of 100 µl of the calibrator and sample dilutions were pipetted into the anti-Fb-½ coated wells of the microtitre plates. After incubation for 30 minutes at between 4° C. and 8° C. the plates were washed four times with 250 µl PBST. Then 100 µl aliquots of the G8/HRP solution in PBST/BSA were added to the wells and incubated for 45 minutes at between 4° C. and 8° C. After washing the plates four times with 250 µl PBST, 100 µl aliquots of TMB/H₂O₂ substrate were added, and incubated for 20 minutes at ambient temperature. A blue colour developed which turned to yellow when the reaction was stopped by the addition of a 100 µl aliquot of 1M $H_2SO_4$ to each well. The absorbance at 450 nm was read using a multichannel spectrophotometer (Multiskan, Flow Laboratories Ltd., Ayrshire, Scotland). A calibration curve was made by plotting the absorbances against the final soluble fibrin concentrations in the calibrator wells (i.e. 1, 0.5, 0.25, 0.125, 0.0625 µg/ml). The soluble fibrin concentrations in the samples were read from this curve.

Concentrations as low as 0.1 µg/ml in the test are readily measurable. This corresponds with a level of 0.5 µg/ml plasma, since the lowest dilution factor used is five-fold.

Correlation with Other Assays

In order to assess whether, upon treatment of plasma with thrombin, the increases in soluble fibrin concentrations correlated with increases in fibrino-peptide A concentrations, plasma samples were treated with varying concentrations of thrombin (0.05–0.25 NIH/ml) for different lengths of time (2–45 minutes). The thrombin reactions were stopped by addition of 100 µl PPACK (5 mM) per 2 ml plasma. Each sample was then divided into two parts. To one portion of the sample (1 ml), was added 200 µl of the anticoagulant solution included in the test kit for fibrinopeptide A (RIA-mat[R] FPA), the other portion (1 ml) was used to assess the soluble fibrin concentration using the EIA (see above). The values found for soluble fibrin and fibrinopeptide A were corrected for dilutions. The correlation between the amount of released fibrino-peptide A and formed soluble fibrin is very good. The correlation coefficient is 0.998.

With another set of samples the correlation between the EIA results and those of the "COA-SET Fibrin monomer" test was investigated.

The correlation between the soluble fibrin values found with the present EIA and the values found with the assay based upon the stimulatory function of fibrin in the activation of plasminogen by tissue type plasminogen activator (COA SET Fibrin monomer) was also good. (Correlation coefficient is 0.984).

I claim:

1. A method for preparing a composition containing a known amount of soluble fibrin, which is substantially free of fibrinogen, comprising
   (a) diluting normal plasma containing a known fibrinogen concentration with a buffer comprising a sugar alcohol, a sodium bromide, an amino acid, and a preservative; and
   (b) treating the diluted plasma with a fibrinopeptide A releasing compound for two hours, whereby all fibrinogen in the plasma is converted to soluble fibrin.

2. The method of claim 1, which further comprises adding a compound that will inactivate the fibrinopeptide A releasing compound after step (b).

3. The method of claim 1, wherein said buffer contains mannitol as the sugar alcohol, glycine as the amino acid, sodium azide as the preservative, and the fibrinopeptide A releasing compound is an enzyme selected from the group consisting of batroxobin, reptilase and an enzyme from venom of *Agkistrodon rhodostoma* that releases only fibrinopeptides A from fibrinogen.

4. A composition comprising sodium bromide, a sugar alcohol, an amino acid, a preservative, a fibrinopeptide A releasing compound, and a known amount of soluble fibrin substantially free of fibrinogen, the composition made by the method of diluting normal plasma containing a known fibrinogen concentration with a buffer comprising sodium bromide, the sugar alcohol, the amino acid, and the preservative, and treating the diluted plasma with the fibrinopeptide A releasing compound for two hours, whereby all fibrinogen in the plasma is converted to soluble fibrin.

5. The composition of claim 4, further comprising a compound, which is added after said treating step of the method, that inactivates the fibrinopeptide A releasing compound.

6. The composition of claim 4, which is lyophilized.

7. The composition of claim 4, wherein the sugar alcohol is selected from the group consisting of mannitol, glucitol, sorbitol, glycerol and inositol; the preservative is sodium azide; and the amino acid is glycine.

8. The composition of claim 7, wherein the sugar alcohol is mannitol.

9. The composition of claim 7, wherein the concentration of sodium bromide is 1M.

* * * * *